United States Patent
Scherpbier et al.

(10) Patent No.: US 7,908,153 B2
(45) Date of Patent: Mar. 15, 2011

(54) INFECTION CONTROL MANAGEMENT AND WORKFLOW SYSTEM

(75) Inventors: Harm Jacob Scherpbier, Fort Washington, PA (US); Laura Koetter, Phoenixville, PA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 611 days.

(21) Appl. No.: 11/956,499

(22) Filed: Dec. 14, 2007

(65) Prior Publication Data
US 2008/0147443 A1    Jun. 19, 2008

Related U.S. Application Data

(60) Provisional application No. 60/870,214, filed on Dec. 15, 2006.

(51) Int. Cl.
*G06Q 10/00* (2006.01)
*G06Q 50/00* (2006.01)
(52) U.S. Cl. .................. 705/2; 705/3; 600/300
(58) Field of Classification Search .......... 705/2–3; 600/300
See application file for complete search history.

(56) References Cited

U.S. PATENT DOCUMENTS

| 6,991,761 | B2 | 1/2006 | Hehenberger et al. | |
|---|---|---|---|---|
| 7,096,161 | B2 | 8/2006 | Smith et al. | |
| 2005/0075904 | A1* | 4/2005 | Wager et al. | 705/2 |
| 2006/0036619 | A1 | 2/2006 | Fuerst et al. | |
| 2006/0080142 | A1* | 4/2006 | Hart et al. | 705/2 |
| 2010/0280837 | A1* | 11/2010 | Naidich et al. | 705/2 |

* cited by examiner

*Primary Examiner* — Luke Gilligan
(74) *Attorney, Agent, or Firm* — Alexander J Burke

(57) ABSTRACT

A system identifies multiple medical conditions, observations, and laboratory test results using active sensors and predetermined rules to identify infected patients. An infection control and workflow management system includes a repository of worker information identifying healthcare workers for performing infection control tasks as well as worker associated communication data for use in informing healthcare workers of infection control tasks to be performed. A detection processor automatically detects infection in patients from multiple different sources including from at least one of, (a) a medical record evaluated upon admission of a patient to a hospital and (b) a laboratory test result. A workflow processor uses the worker information for automatically communicating a message to inform a healthcare worker of a task to be performed to initiate infection control tasks using communication data in response to detection of an infected patient.

24 Claims, 4 Drawing Sheets

INFECTION CONTROL MANAGEMENT AND WORKFLOW SYSTEM

This is a non-provisional application of provisional application Ser. No. 60/870,214 filed Dec. 15, 2006, by L. Koetter et al.

FIELD OF THE INVENTION

This invention concerns a system for providing automated workflow to identify and manage patients with infections (e.g., MRSA, C-Difficile) as well as other patients and clinicians near infected patients and infected rooms and equipment.

BACKGROUND OF THE INVENTION

The identification, control, and elimination of life threatening bacteria and the infections they provoke among patients in healthcare facilities is a major problem facing healthcare providers. Known systems are manually managed using retrospective information. Consequently infections are identified late which increases the risk of spread of hospital acquired infections and prolongs the infection of the patient who was first infected. Hospital facilities also need to be quarantined and disinfected causing major disruption in hospital operations. A system according to invention principles addresses these deficiencies and related problems.

SUMMARY OF THE INVENTION

A system provides an automated workflow (task sequence) identifying multiple medical conditions, observations, and laboratory test results using predetermined rules to identify infected patients (e.g., with MRSA, C-Difficile), their locations and other patients and clinicians near the infected patient as well as infected rooms and equipment. An infection control and workflow management system includes a repository of worker information identifying healthcare workers for performing infection control tasks as well as worker associated communication data for use in informing healthcare workers of infection control tasks to be performed. A detection processor automatically detects infection in patients from multiple different sources including from at least one of, (a) a record evaluated upon admission of a patient to a hospital and (b) a laboratory test result. A workflow processor uses the worker information for automatically communicating a message to inform a healthcare worker of a task to be performed to initiate infection control tasks using communication data in response to detection of an infected patient.

DETAILED DESCRIPTION OF THE INVENTION

Figure 1:
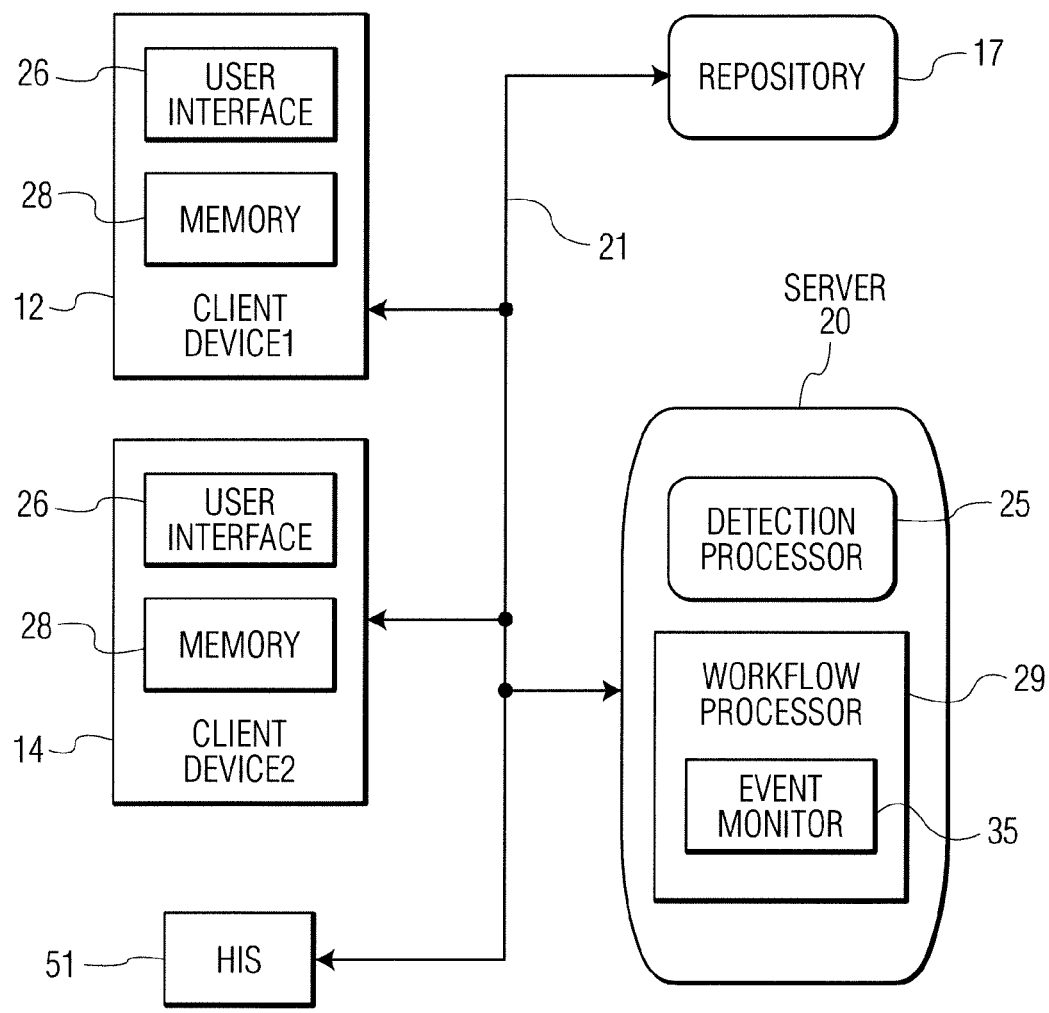
FIG. 1 shows an infection control and workflow management system, according to invention principles.

A system employs an automated workflow method and system employing active infection detection sensors for detecting multiple medical conditions, observations, and results. The system uses predetermined rules to identify infected patients, their locations and other patients and clinicians near the infected patient as well as rooms and equipment that are infected. The system automatically initiates interventions by healthcare workers to isolate an infected patient, initiate treatments to control and manage an infection to reduce the severity of the infection. The system provides data for identifying other patients and clinicians to be monitored for infection in case of spread of the infection and provides statistical information required to report hospital-acquired infections for regulatory organizations, such as JCAHO (Joint Commission on Accreditation of Healthcare Organizations) and hospital infection control review boards. The system increases safety of patients susceptible to infections such as, but not limited to, VRE, *C. difficile*, MRSA (Vaancomycin Resistant Enterococcus, *Clostridium Difficile*, Methicillin Resistant *Staphylococcus aureus*), and others. These infections require multiple interventions to control the infection and to prevent other patients from acquiring the infection.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor may comprise a combination of, hardware, firmware, and/or software.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps (e.g., of FIG. 1) herein may be performed automatically or wholly or partially in response to user command. An activity (including a step)

performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure.

A workflow processor, as used herein, processes data to determine tasks to add to a task list, remove from a task list or modifies tasks incorporated on, or for incorporation on, a task list. A task list is a list of tasks for performance by a worker or device or a combination of both. A workflow processor may or may not employ a workflow engine. A workflow engine, as used herein, is a processor executing in response to predetermined process definitions that implement processes responsive to events and event associated data. The workflow engine implements processes in sequence and/or concurrently, responsive to event associated data to determine tasks for performance by a device and or worker and for updating task lists of a device and a worker to include determined tasks. A process definition is definable by a user and comprises a sequence of process steps including one or more, of start, wait, decision and task allocation steps for performance by a device and or worker, for example. An event is an occurrence affecting operation of a process implemented using a process definition. The workflow engine includes a process definition function that allows users to define a process that is to be followed and includes an Event Monitor, which captures events occurring in a Healthcare Information System. A processor in the workflow engine tracks which processes are running, for which patients, and what step needs to be executed next, according to a process definition and includes a procedure for notifying clinicians of a task to be performed, through their worklists (task lists) and a procedure for allocating and assigning tasks to specific users or specific teams. A document or record comprises a compilation of data in electronic form and is the equivalent of a paper document and may comprise a single, self-contained unit of information.

FIG. 1 shows infection control and workflow management system 10. System 10 identifies patients with C-Difficile, VRE or MRSA infections and includes client devices (workstations) 12 and 14, repository 17, hospital information system (HIS) 51 and server 20 intercommunicating via network 21. Workstations (client devices) 12 and 14 individually include memory 28 and a user interface 26. User interface 26 provides data representing display images for presentation on workstation 12 and 14. Repository 17 includes worker information identifying healthcare workers for performing infection control tasks as well as worker associated communication data for use in informing healthcare workers of infection control tasks to be performed. Repository 17 also includes data identifying clinicians, rooms and equipment (and their locations) potentially infected as a result of infection of the patient. Detection processor 25 automatically detects infection in patients from data in at least one of, (a) a record generated upon admission of a patient to a hospital, (b) a laboratory test result, (c) an infection detection sensor located in a hospital and (d) a patient medical record data, by searching the data for indication of infection or a history of infections.

Workflow processor 29 uses the worker information for automatically communicating a message to inform a healthcare worker of a task to be performed to initiate infection control tasks using communication data in response to detection of an infected patient. The infection control tasks include patient isolation procedures. The message informing the healthcare worker of the task to be performed to initiate infection control comprises a message for adding a task to a worker task list.

Workflow processor 29 automatically communicates multiple messages to inform corresponding multiple healthcare workers of tasks to be added to worker task lists indicating tasks to be performed to initiate infection control tasks in response to detection of an infected patient. Thereby, workflow processor 29 provides automatic notification of actions to be taken to an infection control team via a Clinical Information System (CIS) worklist, for example. The multiple healthcare workers comprise a nurse, a physician, a central supplies manager, an infection control coordinator and a cleaning and disinfection worker. The workflow processor 29 is user configurable to notify additional healthcare workers. Workflow processor 29 executes in response to predetermined process definitions to determine tasks to add to a worker task list and manage processes responsive to events comprising detection of infection in a patient based on, (a) the record generated upon admission of the patient to the hospital and (b) the laboratory test result.

Workflow processor 29 includes event monitor 35 for identifying the events, using data from Hospital Information System 51. Workflow processor 29 tracks different concurrent infection control processes for corresponding different patients and steps to be executed next in response to a process definition. Workflow processor 29 automatically communicates a message to add workers to implement infection control tasks in response to detection of an infected patient. Detection processor 25 automatically detects an indication a patient is not infected in response to a laboratory test: result and workflow processor 29 automatically communicates a message to inform a healthcare worker infection control procedures for a patient may be terminated in response to detection of the indication the patient is not infected. Detection processor 25 automatically detects infection from data indicating patient medical conditions and clinical observations.

Figure 2:
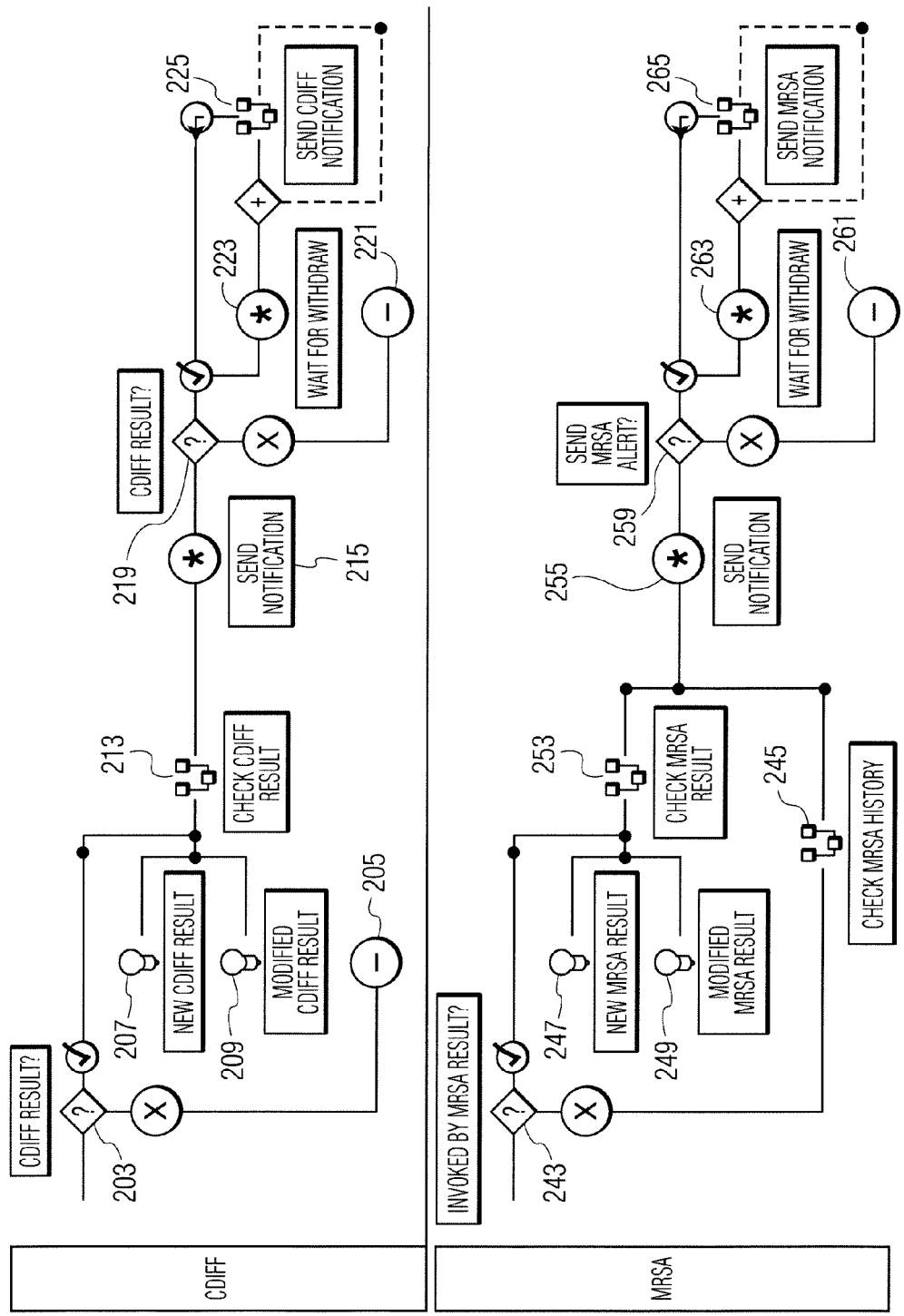
FIG. 2 shows an infection control workflow for automatically alerting infection control staff, according to invention principles.

FIG. 2 illustrates an infection control workflow process definition employed by workflow processor 29 for automatically alerting infection control staff. The workflow process is initiated in response to determining if a C. Difficile test result is detected in a patient laboratory test result in step 203. If no C. Difficile result is detected, the process terminates in step 205. Items 207 and 209 indicate workflow processor 29 continuously monitors events for a new C. Difficile infection test result 207 or a modified test result 209 (e.g., following a re-test for confirmation). If step 203 is true, or events trigger steps 207 or 209, workflow processor 29 initiates checking the C. Difficile infection test result in step 213. For this purpose, workflow processor 29 executes a series of rules, matching the results of a test against pre-set infection representative values and value ranges in a lookup table, for example. Since individual hospital infection representative test values may vary, the rule logic is adjustable for an individual organization. The results of executing the rules comprise a yes/no decision about whether a patient should be placed in isolation based on incoming patient test data.

Step 215 indicates start of notification procedures. In step 219 workflow processor 29 assesses a need to notify health workers to place a patient in isolation based on the output of step 213. If it is determined there is no need for isolation, the process ends in step 221. If it is determined isolation is required, a notification procedure is initiated in step 225. If the workflow process is executing again based on new information, following a new or modified result event (207 or 209), previous notifications to healthcare workers are withdrawn (supported by step 223) and replaced with updated information in step 225. For example, if the patient was previously determined to have the infection and notification to isolate the patient was communicated, and a new result is negative, notification to remove isolation measures is communicated. In response to confirming a C. Difficile infection test result, workflow processor 29 in step 225 automatically communicates multiple messages to inform corresponding multiple healthcare workers of tasks to be performed to initiate infection control in response to detection of an infected patient. Workflow processor 29 initiates automatic notifications, where appropriate, via pager, email, voicemail, phone or printing forms, for example.

In one embodiment, the multiple messages comprise messages adding tasks to worker task lists, prompting workers to initiate infection control in response to detection of an infected patient. The multiple healthcare workers comprise a nurse, a physician a central supplies manager, an infection control coordinator, a cleaning and disinfection worker, housekeeping and a dietary department or hospital kitchen, for example. Similarly, a workflow process is initiated in response to determining if a MRSA test result is detected in a patient laboratory test result in step 243. Workflow processor 29 in steps 247 and 249 continuously monitors events for a new MRSA test result 247 or a modified test result 249 (e.g., following a re-test for confirmation). If step 243 is true, or events trigger steps 247 or 249, workflow processor 29 initiates checking the MRSA infection test result in step 253. For this purpose workflow, processor 29 executes a series of rules, matching the results of the test against pre-set comparison values representative of infection in a look-up table, for example. Since individual hospital infection representative test values may vary, the rule logic is adjustable for an individual organization. The results of executing the rules comprise a yes/no decision about whether a patient should be placed in isolation based on incoming patient test data.

Step 255 indicates start of notification procedures. In step 259 workflow processor 29 assesses a need to notify health workers to place a patient in isolation based on the output of step 253. If it is determined there is no need for isolation, the process ends in step 261. If it is determined isolation is required, a notification procedure is initiated in step 265. If the workflow process is executing again based on new information, following a new or modified result event (247 or 249), previous notifications to healthcare workers are withdrawn (supported by step 263) and replaced with the updated information in step 265. For example, if the patient was previously determined to have the infection and notification to isolate the patient was communicated, and a new result is negative, notification to remove isolation measures is communicated. Further, workflow processor 29, in the absence of a MRSA test result being detected in step 243, initiates examination of the medical history and records of an admitted patient to determine if the patient has previously had, or been exposed to, MRSA in step 245. In response to confirming a MRSA infection test result or upon examination of the medical history of an admitted patient and determining a patient has a history of MRSA or been exposed to MRSA, workflow processor 29 in step 265 automatically communicates multiple messages to inform corresponding multiple healthcare workers of tasks to be performed to initiate infection control. The multiple messages comprise messages adding tasks to worker task lists (or alternatively just informing workers), prompting workers to initiate infection control in response to detection of an infected patient.

Figure 3:
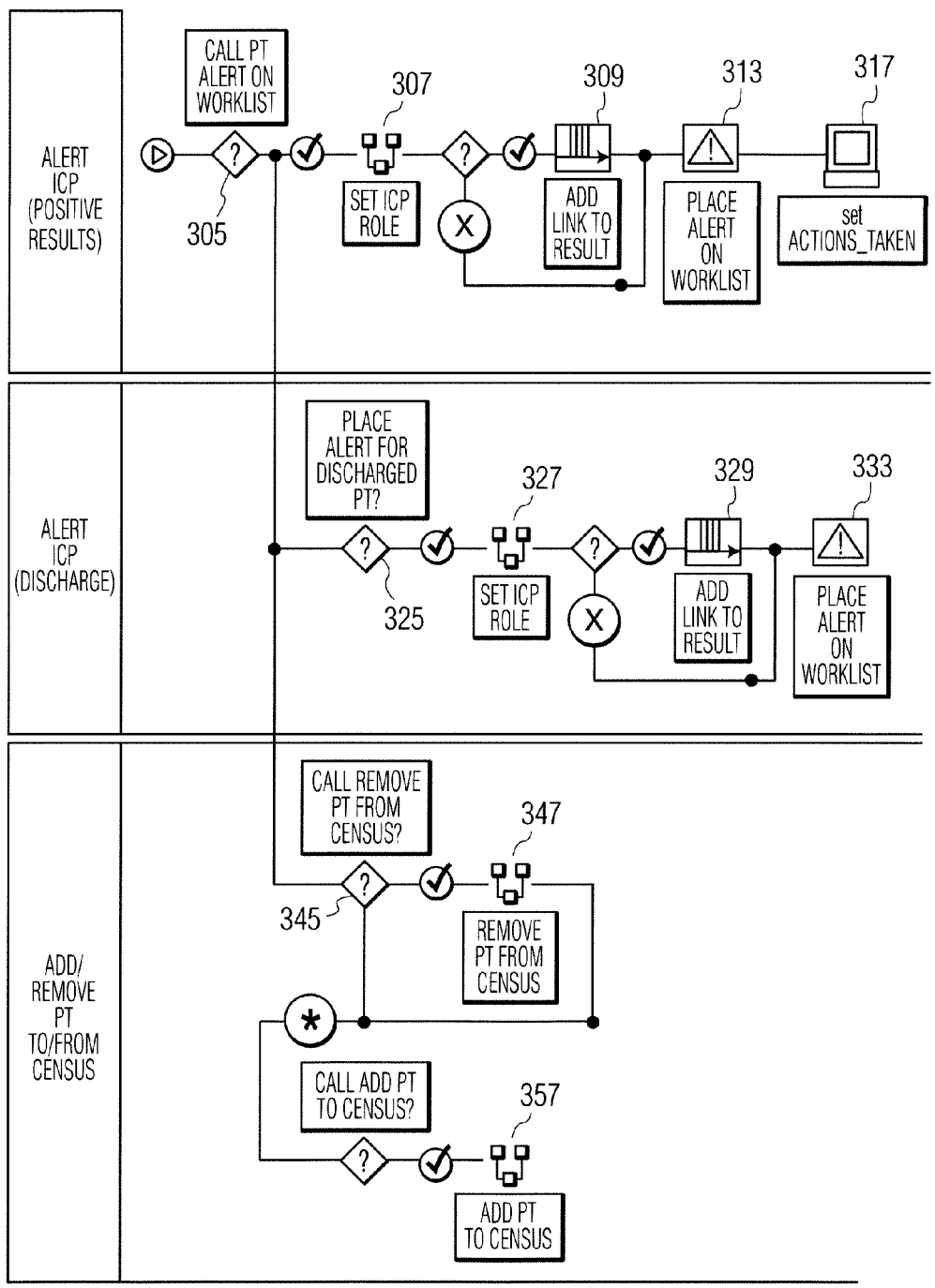
FIG. 3 shows an infection control workflow for automatically alerting infection control staff according to invention principles.

FIG. 3 is a notification process, initiated by steps 225 and 265 (and similar steps for other organisms). FIG. 3 shows the section of the infection control workflow responsible for automatically alerting infection control staff. Following the start at step 303, in response to a determination in step 305 to add an alert or task to a worker task list, the FIG. 3 workflow is configured to alert personnel of selected roles in step 307. In step 309 a link is provided in task (or alert) data to be added to a task list of workers having the roles selected in step 307. The link is to laboratory test result data indicating an infection or to a patient record indicating a history of previous infection or indicating exposure to infection. In step 313, the task (or alert) data is added to task lists of workers having the roles selected in step 307. The task and alert actions taken are recorded in step 317.

Further, following the start at step 303, in response to a determination in step 325 to add an alert or task to a worker task list concerning a discharged patient, the FIG. 3 workflow is configured to alert personnel of selected roles in step 327. In step 329 a link is provided in task (or alert) data to be added to a task list of workers having the roles selected in step 327. The link is to laboratory test result data indicating an infection or to a patient record indicating a history of previous infection or indicating exposure to infection. In step 333, the task (or alert) data is added to task lists of workers having the roles selected in step 327. An alert following discharge does not require initiation of infection control procedures for the patient. Actions taken are not recorded.

Also, following the star at step 303, patients are added or removed from worklists of workers indicated in a working census list of healthcare workers. A census is a list of patients of interest to the healthcare worker. For example, an infection control nurse census would includes patients with a positive infection in the hospital that the nurse manages. In response to a determination in step 355 to add a patient to a census list of one or more selected infection control workers, the patient is added to the appropriate census lists in step 357. The determination in step 355 to add a patient to a census list of one or more healthcare workers is made automatically in response to a positive infection test result, for example, or in response to a record generated upon admission of a patient to a hospital, a search of a patient medical record history indicating infection or data provided by an infection detection sensor located in a hospital. Thereby, in response to detection of a patient infection, an alert message is sent to an Infection Control worker (e.g., a nurse) and the patient is added to the census list of the worker. In response to a determination in step 345 to remove a patient from a census list of one or more selected infection control workers, the patient is removed from the appropriate census lists in step 347. The determination in step 345 to remove a patient from a census list of one or more infection control workers is made automatically in response to a negative infection test result, for example, or upon patient discharge from the hospital. System 10 continuously monitors for negative cultures and laboratory test results. In response to detecting a negative infection test result, workflow processor 29 initiates discontinuation of isolation precautions and lifts the contact and quarantine precautions.

In addition to evaluating current results, the automated workflow process implemented by processor 29 checks for a history of positive MRSA or VRE in the past 6 months, for example, upon patient admission to a healthcare facility. This evaluation of a medical history of infection upon admission identifies Inpatients and Pre-Admission patients before the patient is placed in (and contaminates) a room. System 10 provides automatic and workflow-driven detection of new MRSA cases (through a link to laboratory test data, for example), and previous existing MRSA cases (by looking at previous patient encounters with a healthcare provider organization). System 10 also does this for other bacteria: VRE, C.

*difficile*, and others (Vancomycin Resistant Enterococcus, and *Clostridium difficile*). System 10 automatically initiates isolation precautions as well as provides subsequent notifications (replacing numerous phone calls). System 10 automatically initiates adjustment to work shifts and special procedures for weekends and times of low staffing in response to infection detection.

Figure 4:
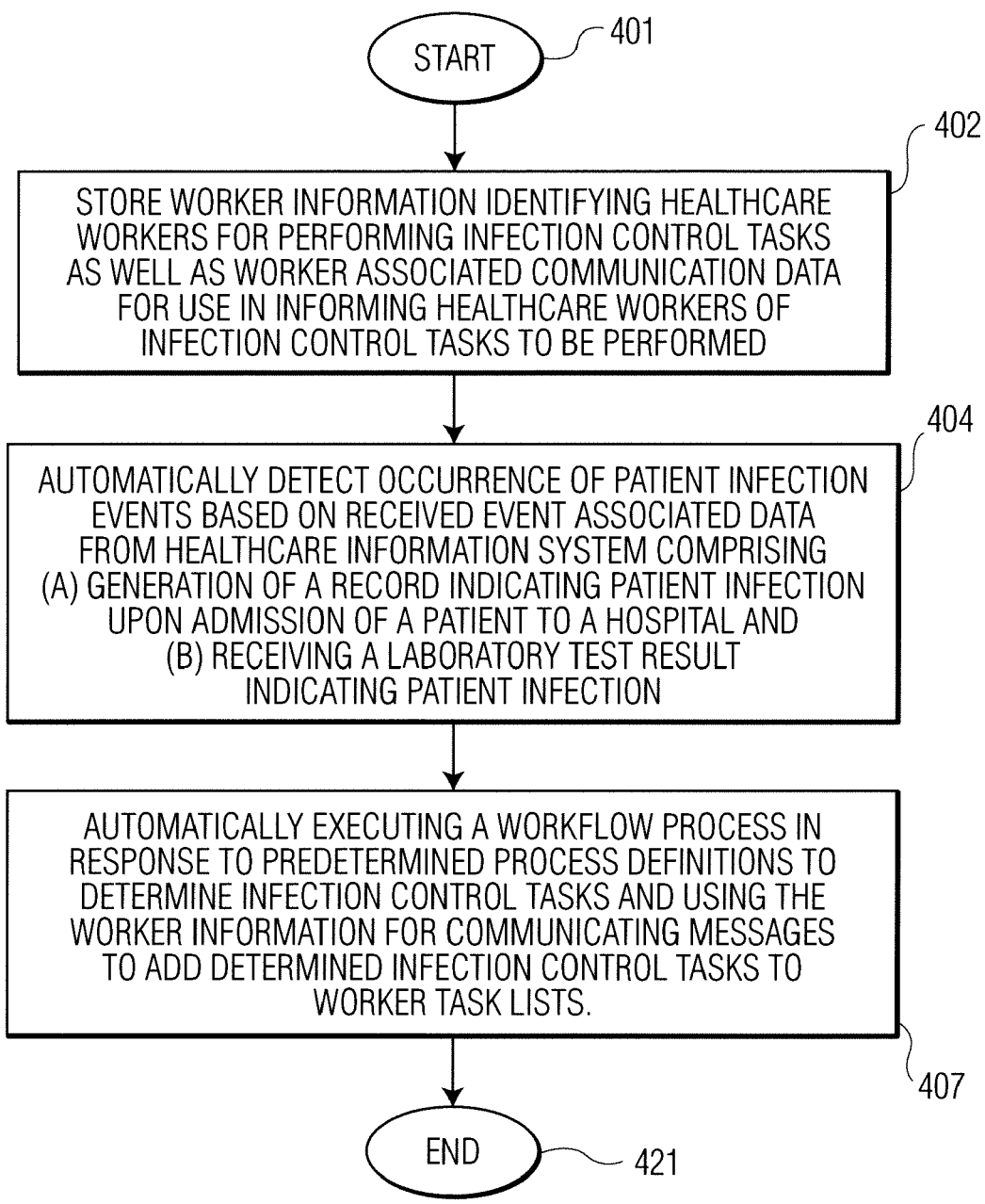
FIG. 4 shows a flowchart of a process for performing infection control and workflow management, according to invention principles.

FIG. 4 shows a flowchart of a process for performing infection control and workflow management. In step 402 following the start at step 401, system 10 stores worker information in repository 17 identifying healthcare workers for performing infection control tasks as well as worker associated communication data for use in informing healthcare workers of infection control tasks to be performed. In step 404, detection processor 25 automatically detects patient infection events comprising, generation of a record indicating patient infection upon admission of a patient to a hospital and receiving a laboratory test result indicating patient infection. Detection processor 25 automatically detects infection in patients from data in a patient medical record and a laboratory test result as well as from a record generated upon admission of a patient to a hospital and from data from an infection detection sensor located in a hospital. Workflow processor 29 includes event monitor 35 for detecting occurrence of the events based on received event associated data from healthcare information system 51. In step 407, workflow processor 29 automatically executes in response to predetermined process definitions to determine infection control tasks and uses the worker information for communicating messages to add determined infection control tasks to worker task lists.

Workflow processor 29 manages infection control processes responsive to the events and executes in response to predetermined process definitions determining, a sequence of process steps including, (a) start, (b) wait, (c) decision and (d) task allocation steps. A predetermined process definition determines a sequence of process steps to add, a task to a worker task list, to remove a task from a worker task list and to modify a task on a worker task list. Further, workflow processor 29 uses the worker information for automatically communicating a message to add a task to a worker task list such as a task to implement an infection control procedure, using communication data in response to detection of an infected patient. The infection control procedure includes a patient isolation procedure. The process of FIG. 4 terminates at step 421.

The systems and processes of FIGS. 1-4 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A Healthcare organization is able to customize and change the described infection control workflows, and to accommodate the fact that one hospital is different from another, and an individual hospital is able to tailor the process to their individual situation. A process used today may be different from the process used tomorrow (new data, new rules, new tasks for workers, etc), and through the ability to change the workflow, the process can be kept up to date and current. System 10 is usable for infection control and workflow management in any type of healthcare facility. The processes and applications may in alternative embodiments, be located on one or more (e.g., distributed) processing devices accessing a network linking the elements, of FIG. 1. Further, any of the functions and steps provided in FIGS. 1-4 may be implemented in hardware, software or a combination of both and may reside on one or more processing devices located at any location of a network linking the elements of FIG. 1 or another linked network including the Internet.

What is claimed is:

1. An infection control and workflow management system, comprising:
    a repository including worker information identifying healthcare workers for performing infection control tasks as well as worker associated communication data for use in informing healthcare workers of infection control tasks to be performed;
    at least one processing device comprising,
    a detection processor for automatically detecting infection in patients from data in at least one of, (a) a patient medical record accessed upon admission of a patient to a hospital and (b) a laboratory test result; and
    a workflow processor including
        an event monitor for identifying events comprising detection of infection, using data from a hospital information system, said workflow processor
        using said worker information for automatically communicating a message to inform a healthcare worker of a task to be performed to initiate infection control tasks of an infection control process using communication data in response to at least one of, the detection of an infected patient and the identified event and
        automatically tracking different concurrent infection control processes for corresponding different patients and determining steps to be executed next by at least one of said healthcare workers.

2. A system according to claim 1, including
    a repository including data identifying clinicians, rooms and equipment potentially infected as a result of infection of said patient wherein
    said infection control tasks include patient isolation procedures and
    said detection processor automatically detects infection in patients from patient medical record data by searching the medical record for a history of infections.

3. A system according to claim 1, wherein
    said detection processor automatically detects infection in patients from data provided by an infection detection sensor located in a hospital.

4. A system according to claim 1, wherein
    said message informing said healthcare worker of said task to be performed to initiate infection control tasks comprises a message for adding a task to a worker task list and including
    a repository including data identifying clinicians, rooms and equipment potentially infected as a result of infection of said patient and
    said workflow processor communicates a message to inform a healthcare worker of a task to be performed to initiate isolation of one or more of said clinicians, rooms and equipment.

5. A system according to claim 1, wherein
    said workflow processor automatically communicates a plurality of messages to inform a corresponding plurality of healthcare workers of tasks to be performed to initiate infection control in response to detection of an infected patient.

6. A system according to claim 5, wherein
said plurality of messages comprise messages adding tasks to worker task lists prompting workers to initiate infection control in response to detection of an infected patient.

7. A system according to claim 5, wherein
said plurality of healthcare workers comprise at least one of, (a) a nurse, (b) a physician, (c) a central supplies manager, (d) an infection control coordinator and (e) a cleaning and disinfection worker.

8. A system according to claim 5, wherein
said workflow processor executes in response to predetermined process definitions to determine tasks to add to a worker task list and manage processes responsive to events comprising detection of infection in a patient based on,
a) said record accessed upon admission of said patient to said hospital and
(b) said laboratory test result.

9. A system according to claim 8, wherein
said workflow processor includes an event monitor for substantially continuously monitoring for events comprising an infection test result identifying a predetermined particular type of infection.

10. A system according to claim 9, wherein
said workflow processor tracks different concurrent infection control processes for corresponding different patients and steps to be executed next in response to a process definition.

11. A system according to claim 1, wherein
said workflow processor automatically communicates a message to add workers to implement infection control tasks in response to detection of an infected patient.

12. A system according to claim 1, wherein
said detection processor automatically detects an indication a patient is not infected in response to a laboratory test result and
said workflow processor automatically communicates a message to inform a healthcare worker infection control procedures for a patient may be terminated in response to detection of said indication said patient is not infected.

13. A system according to claim 1, wherein
said detection processor automatically detects infection from data indicating patient medical conditions and clinical observations.

14. A system according to claim 1, wherein
said repository includes data identifying clinicians, rooms and equipment potentially infected as a result of infection of said patient and
said workflow processor communicates a message to inform a healthcare worker of a task to be performed to initiate isolation of one or more of said clinicians, rooms and equipment.

15. A system according to claim 14, wherein
said repository includes data identifying locations of rooms and equipment and
said workflow processor communicates a message to inform a healthcare worker of said locations.

16. An infection control and workflow management system, comprising:
a repository including worker information identifying healthcare workers for performing infection control tasks as well as worker associated communication data for use in informing healthcare workers of infection control tasks to be performed;
at least one processing device comprising,
a detection processor for automatically detecting patient infection events comprising (a) generation of a record indicating patient infection upon admission of a patient to a hospital and (b) receiving a laboratory test result indicating patient infection; and
a workflow processor for automatically executing in response to predetermined process definitions to determine infection control tasks and using said worker information for communicating messages to add determined infection control tasks to worker task lists, said workflow processor substantially continuously monitoring for events comprising an infection test result identifying a predetermined particular type of infection and including
an event monitor for identifying events comprising detection of infection, using data from a hospital information system and
using said worker information for automatically communicating a message to inform a healthcare worker of a task to be performed to initiate infection control tasks of an infection control process using communication data in response to at least one of, the detection of an infected patient and the identified event and
automatically tracking different concurrent infection control processes for corresponding different patients and determining steps to be executed next by at least one of said healthcare workers.

17. A system according to claim 16, wherein
said workflow processor manages infection control processes responsive to said events.

18. A system according to claim 16, including
an event monitor for detecting occurrence of said events based on received event associated data from a healthcare information system.

19. A system according to claim 16, wherein
said workflow processor executes in response to predetermined process definitions determining a sequence of process steps including two or more of, (a) start, (b) wait, (c) decision and (d) task allocation steps.

20. A system according to claim 16, wherein
said workflow processor executes in response to a predetermined process definition determining a sequence of process steps to add, a task to a worker task list and to remove a task from a worker task list.

21. A system according to claim 20, wherein
said workflow task processor executes in response to a predetermined process definition determining a sequence of process steps to modify a task on a worker task list.

22. An infection control and workflow management system, comprising:
a repository including worker information identifying healthcare workers for performing infection control tasks as well as worker associated communication data for use in informing healthcare workers of infection control tasks to be performed;
at least one processing device comprising,
a detection processor for automatically detecting infection in patients from data in (a) a patient medical record and (b) a laboratory test result; and
a workflow processor for using said worker information for automatically communicating a message to add a task to a worker task list, said task being to implement an infection control procedure, using communication data in response to detection of an infected patient, said workflow processor substantially continuously monitoring for events comprising an infection test result identifying a predetermined particular type of infection and including an event monitor for identifying events comprising detection of infection, using data from a hospital information system and using said worker information for automatically communicating a message to inform a healthcare worker of a task to be performed to initiate infection control tasks of an infection control process using communication data in response to at least one of, the detection of an infected patient and the identified event and automatically tracking different concurrent infection control processes for corresponding different patients and determining steps to be executed next by at least one of said healthcare workers.

23. A system according to claim 22, including a repository including data identifying clinicians, rooms and equipment potentially infected as a result of infection of said patient wherein said detection processor automatically detects infection in patients from a record generated upon admission of a patient to a hospital and and said infection control procedure includes a patient isolation procedure.

24. A system according to claim 23, wherein said detection processor automatically detects infection in patients from data from an infection detection sensor located in a hospital.

* * * * *